(12) United States Patent
Tanaka

(10) Patent No.: US 8,748,698 B2
(45) Date of Patent: Jun. 10, 2014

(54) GENOME SHUFFLING METHOD FOR AUTOGAMOUS PLANTS UTILIZING DOMINANT MALE STERILITY OBTAINED BY GENE ENGINEERING TECHNIQUE, AND RECURRENT SELECTION BREEDING SYSTEM BASED ON THE GENOME SHUFFLING METHOD

(71) Applicant: Junichi Tanaka, Ushiku (JP)

(72) Inventor: Junichi Tanaka, Ushiku (JP)

( * ) Notice: Subject to any disclaimer, the term of this patent is extended or adjusted under 35 U.S.C. 154(b) by 0 days.

(21) Appl. No.: 14/101,913

(22) Filed: Dec. 10, 2013

(65) Prior Publication Data

US 2014/0101788 A1 Apr. 10, 2014

Related U.S. Application Data

(60) Division of application No. 12/915,633, filed on Oct. 29, 2010, now Pat. No. 8,629,322, which is a continuation of application No. PCT/JP2009/052176, filed on Feb. 9, 2009.

(30) Foreign Application Priority Data

Apr. 30, 2008 (JP) ................. 2008-140136

(51) Int. Cl.
 *C07K 14/415* (2006.01)
 *A01H 5/10* (2006.01)
 *C12N 9/22* (2006.01)

(52) U.S. Cl.
 USPC ........... 800/278; 800/260; 800/274; 800/294; 800/300; 800/303; 800/267; 435/199

(58) Field of Classification Search
 CPC ............. C12N 15/8275; C12N 9/1029; C12N 15/8261; C12N 15/8269; C12N 9/0036; C12N 9/88; C12N 15/10; C12N 15/1027; C12N 15/8216; C12N 15/8274; C12N 15/8279; C12N 15/8289; C12N 9/0008; C12N 9/12; C12N 9/1205; C12N 9/14; C12N 9/16; C07K 14/41; C07K 14/415; C07K 14/47; C07K 14/245; C07K 14/325; C07K 14/20; C07K 2319/40; C07K 14/4702; C07K 14/575; C07K 14/5759; C07K 14/705; C07K 16/12
 See application file for complete search history.

(56) References Cited

U.S. PATENT DOCUMENTS

| | | |
|---|---|---|
| 4,658,084 A | 4/1987 | Beversdorf et al. |
| 5,254,801 A | 10/1993 | Dotson et al. |
| 6,204,061 B1 | 3/2001 | Capecchi et al. |
| 6,509,516 B1 | 1/2003 | Weston et al. |

FOREIGN PATENT DOCUMENTS

| | | |
|---|---|---|
| EP | 0198288 | 10/1986 |
| JP | 2000-037146 | 2/2000 |

OTHER PUBLICATIONS

Wilson et al., "Dynamic Multiline Population Approach to Resistance Gene Management," Phytopathology, 2000, vol. 91, No. 3, pp. 255-260.
Knapp et al., "$S_1$ Family Recurrent Selection in Autogamous Crops Based on Dominant Genetic Male-Sterility," Crop Sci., vol. 28, 1988, pp. 227-231.
Ramage, "Techniques for Producing Hybrid Barley," Barley Newsletter, 1975, vol. 18, pp. 62-65.
Eslick, "Male Sterile Facilitated Recurrent Selection-Advantages and Disadvantages," Proc. $4^{th}$ Regional Winter Cereals Workshop (Barley), 1977, vol. 2, pp. 94-91.
Mariani et al., "Induction of male sterility in plants by a chimaeric ribonuclease Gene," Nature, 1990, vol. 347, pp. 737-741.
Mariani et al., "A chimaeric ribonuclease-inhibitor gene restores fertility to male sterile plants," Nature, 1992, vol. 357, pp. 384-387.
Kobayashi et al., "A conditional negative selection for Arabidopsis expressing a bacterial cytosine deaminase gene," Japanese Journal of Genetics, 1995, vol. 70, pp. 409-422.
Koprek et al., "Negative selection systems for transgenic barley (*Hordeum vulgare* L.): comparison of bacterial codA- and cytochrome P450 gene-mediated selection," The Plant Journal, 1999, vol. 19, No. 6, pp. 719-726.
Ramage (Classical vs. Recurrent Selection Breeding Approaches for Developing Disease Resistance, pp. 115-121, in Proceedings of a Symposium: Biotic Stress of Barley pp. 1-196, (Jul. 31-Aug. 2, 1990)).

*Primary Examiner* — Brent T Page
*Assistant Examiner* — Jared Shapiro
(74) *Attorney, Agent, or Firm* — Hamre, Schumann, Mueller & Larson, P.C.

(57) ABSTRACT

A genome shuffling method for autogamous plants, including producing individuals having the following three traits in a tight coupling linkage by a gene engineering technique selected from a transgenic technique and a gene targeting technique: 1) dominant male sterility, 2) chemical tolerance and 3) lethality inducible by activating an inducible promoter, selecting, from progeny of the individuals, male-sterile individuals by means of the chemical tolerance described in 2) and male-fertile individuals by means of the lethality described in 3), arranging the male-sterile individuals and the male-fertile individuals close together in flowering periods thereof, so that the male-sterile individuals are crossed with the male-fertile individuals, harvesting seeds from the male-sterile individuals, and repeating outcrossing using the seeds from generation to generation.

1 Claim, 2 Drawing Sheets

GENOME SHUFFLING METHOD FOR AUTOGAMOUS PLANTS UTILIZING DOMINANT MALE STERILITY OBTAINED BY GENE ENGINEERING TECHNIQUE, AND RECURRENT SELECTION BREEDING SYSTEM BASED ON THE GENOME SHUFFLING METHOD

CROSS-REFERENCE TO RELATED APPLICATION

This is a continuation application of PCT/JP2009/052176, filed on Feb. 9, 2009.

BACKGROUND OF THE INVENTION

1. Field of the Invention

The present invention relates to a technique for realizing genome shuffling by efficiently repeating outcrossing of plants that are usually self-pollinating such as rice and wheat (i.e., autogamous plants) without involving laborious procedures such as emasculation and identification of male-sterile individuals; and to an efficient recurrent selection breeding system based on the technique.

2. Description of the Related Art

Breeding of allogamous plants such as corn originally involves recurrent selection. Specifically, genome shuffling is caused due to frequent genetic recombination between homologous chromosomes of heterozygotes and increases genetic variability, enhancing breeding effects.

Meanwhile, for the production of cultivars in autogamous plants such as rice and wheat, selfing is generally repeated from the juvenile screening stage and thus fixed strains are selected. Therefore, frequent genetic recombination can be observed in only a few generations, which perhaps impose limitation on the breeding of autogamous plants.

Primarily, the breeding effects depend greatly on "increased variability through genetic recombination between numerous alleles" and "applying appropriate, continuous selection pressure to a population." Thus, an ideal breeding system is a recurrent selection breeding system that can perform efficient genome shuffling and also apply strong selection pressure to a large population.

Nuclear male sterility is effectively utilized for realizing recurrent selection based on genome shuffling which is achieved by efficiently outcrossing autogamous plants. As a method for realizing such recurrent selection, the MSFRS (Male Sterile Facilitated Recurrent Selection) method is proposed (see Ramage, R. T. (1975) Techniques for producing hybrid barley. Barley Newsl. 18: 62-65; and Eslick, R. F. (1977) Male sterile facilitated recurrent selection-advantages and disadvantages. Proc. 4th Regional Winter Cereals Workshop (Barley). Vol. II. 84-91). The MSFRS method aims to realize recurrent selection based on efficient genome shuffling and to obtain high breeding effects. Specifically, the MSFRS method includes the following steps: 1) selecting male-sterile individuals or male-fertile individuals from a population containing both the male-sterile and male-fertile individuals and producing $F_1$ population by crossing together the selected male-sterile individuals and the selected male-fertile individuals, 2) producing a population of $F_2$ individuals for the next selection cycle, 3) introducing new genetic resources into a population in each cycle through outcrossing with male-sterile individuals, and 4) repeating the selection cycle.

However, the MSFRS method requires discrimination between male-sterile individuals and male-fertile individuals during the flowering period. Thus, the MSFRS method is difficult to use when recurrent selection is efficiently performed in large populations. To resolve this problem, it has been proposed to use, as a marker trait, a seed trait linked with male sterility, for example. However, this method cannot be a universal method since the male-sterile gene must be linked closely with the marker gene. In addition, this method possesses a problem in that the linkage between the marker gene and the male-sterile gene are sometimes broken as a result of genetic recombination therebetween.

Furthermore, other literatures have reported a method in which dominant male-sterile individuals are produced utilizing an anther-specific promoter and a lethal gene (e.g., a ribonuclease-encoding gene) by the transgenic technique (see, for example, U.S. Pat. No. 6,509,516; Mariani, C., M. De Beuckeleer, J. Truettver, J. Leemans, and R. B. Goldberg (1990) Induction of male sterility in plants by a chimaeric endonuclease gene. Nature. 347: 737-741; and Mariani, C., V. Gossele, M. De Beuckeleer, M. De Block, R. B. Goldberg, W. De Greef, and J. Leemans. 1992. A chimaeric ribonuclease-inhibitor gene restores fertility to male sterile plants. Nature (London) 357: 384-387). Also, by introducing a chemical tolerance marker gene (e.g., an herbicide-tolerance marker gene) as the same construct, dominant male-sterile individuals can be selected at the seedling stage. The thus-produced transformants have dominant male sterility and herbicide tolerance in a tight coupling linkage. This method is used for producing $F_1$ seeds of *Brassica napus* L. in North America.

BRIEF SUMMARY OF THE INVENTION

The present invention aims to provide a method for realizing an efficient recurrent selection breeding system for autogamous plants such as rice and wheat which are usually difficult to outcross efficiently. The method achieves genome shuffling by efficiently outcrossing large populations of the autogamous plants, and involves no discrimination between male-sterile and male-fertile individuals during the flowering period although the MSFRS method requires such discrimination.

DETAILED DESCRIPTION OF THE INVENTION

Figure 1:
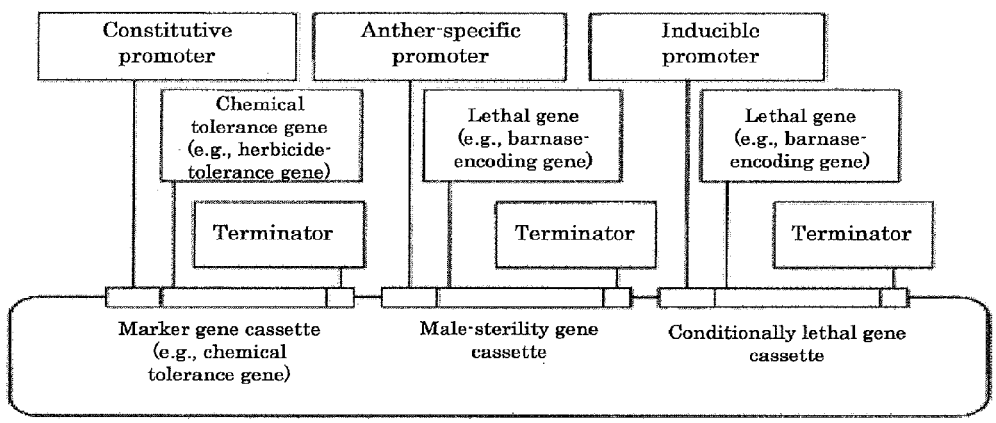
FIG. 1 schematically illustrates one exemplary vector containing 1) a male-sterility gene cassette, 2) a chemical tolerance gene cassette and 3) a conditionally lethal gene cassette as a single construct.

One feature of the present invention to solve the above existing problems is to utilize dominant male sterility obtained by a gene engineering technique such as a transgenic technique and a gene targeting technique. Specifically, a vector having the following three gene cassettes as a single construct is used for transformation by a gene engineering technique such as a transgenic technique and a gene targeting technique:

1) a male-sterility gene cassette including an anther-specific promoter and a lethal gene such as a ribonuclease-encoding gene driven by the anther-specific promoter, 2) a chemical tolerance gene cassette including a constitutive promoter and a chemical tolerance gene driven by the constitutive promoter, which allows expression of genes in stems and leaves, and
3) a conditionally lethal gene cassette including an inducible promoter and a lethal gene such as a ribonuclease-encoding gene driven by the inducible promoter, to thereby produce individuals possessing the following three traits in a tight coupling linkage (at almost the same locus):
1) dominant male sterility,
2) chemical tolerance, and
3) lethality inducible by activating the inducible promoter. These traits are dominantly inherited in terms of genetics.

Notably, the lethality inducible by activating the inducible promoter (described in the above 3)); i.e., inducible lethality, can be replaced with susceptibility to physical environment or a specific chemical. Such susceptibility can be given to plants by destroying their intrinsic tolerances to the environment or chemicals by means of, for example, an RNAi-based technique.

The transformants obtained by a gene engineering technique are preferably screened, as usually performed, for individuals that stably express all the traits of interest and have the transgenes inserted at one part of the host genome using a technique such as southern hybridization. The "transgenes inserted at one part of the host genome" means that the three traits of interest are practically inherited under the control of a single locus.

Needless to say, dominant male-sterile individuals cannot produce pollen. Thus, maintaining the dominant male-sterile individuals requires pollen of male-fertile individuals. The dominant male-sterile individuals obtained by a gene engineering technique always have a genotype of Msms, where Ms denotes a gene symbol of dominant male sterility under the control of a single locus (ms denotes a gene symbol of recessive male sterility). The male-fertile individuals have a genotype of msms. Crossing between the dominant male-sterile individuals (genotype: Msms) and the male-fertile individuals (genotype: msms) produces a segregation ratio of 1:1 for Msms to msms in theory. In the case where the introduced sequences are present on two or more loci, the ratio of the male-sterile individuals increases while the ratio of the male-fertile individuals decreases. For example, in the case of the two loci, a segregation ratio of 3:1 for Msms to msms is produced.

Transgenic plants with male sterility have been developed and used for $F_1$ seed production in Brassica napus L. in North America. In this development, the below-described selection system is realized. Specifically, by introducing into plants a single construct containing the chemical tolerance gene cassette including a constitutive promoter and a chemical tolerance gene driven by the constitutive promoter, which allows expression of genes in stems and leaves, as well as the male-sterility gene cassette including an anther-specific promoter and a lethal gene such as a ribonuclease-encoding gene driven by the anther-specific promoter, transformants with both the genes in a tight linkage are produced, followed by treating with a chemical such as an herbicide. As a result, the dominant male-sterile individuals (genotype:Msms) can be efficiently selected from the population containing both the dominant male-sterile individuals (genotype:Msms) and the male-fertile individuals (genotype:msms).

Moreover, after introduction into plants of the above construct further containing the conditionally lethal gene cassette including an inducible promoter and a lethal gene such as a ribonuclease-encoding gene driven by the inducible promoter, the plants are treated so that the introduced promoter is activated. As a result, the dominant male-sterile individuals (genotype:Msms) can be efficiently selected from the population containing both the dominant male-sterile individuals (genotype:Msms) and the male-fertile individuals (genotype: msms).

The conditionally lethal gene cassette can be replaced with a gene cassette which destroys the plants' intrinsic tolerances to a specific chemical or physical environment utilizing an RNAi-based technique, a ribozyme-based technique, an anti-sense technique or other techniques. In this case, the promoter used is not necessarily the inducible promoter. When the plants with such a gene cassette are treated with the specific chemical or placed in physical environment, the dominant male-sterile individuals (genotype:Msms) can be efficiently selected, as described above, from the population containing both the dominant male-sterile individuals (genotype:Msms) and the male-fertile individuals (genotype:msms).

Outcrossed seeds can be efficiently obtained by means of coinciding the flowering period of dominant male-sterile individuals with that of male-fertile individuals, arranging the male-sterile individuals and the male-fertile individuals close together for crossing, and harvesting seeds from the male-sterile individuals, without involving laborious procedures such as emasculation.

Repeating the following four steps 2) to 5) achieves repeated outcrossings even in the population of autogamous plants to efficiently shuffle their genomes:
1) harvesting seeds from male-sterile individuals,
2) splitting the seeds into two groups and sowing them,
3) screening for male-sterile individuals (genotype:Msms) from the seedlings of one group, and screening for male-fertile individuals (genotype:msms) from the seedlings of the other group,
4) appropriately arranging both the individuals, and letting them cross with each other, and
5) harvesting seeds from the male-sterile individuals obtained in the above step 4).

New breeding materials can be introduced into the genetic composition of the genome shuffling population as new male-fertile individuals (genotype:msms).

After the seeds have been harvested from the male-sterile individuals, split into two groups and sown, juvenile screening at the seedling stage can also be performed to test for disease tolerance, etc. before or after the screening for the male-sterile individuals or the male-fertile individuals, leading the traits of the population in a desirable direction.

Although juvenile screening is difficult to perform on the cultivation characters of the population, individuals of the next generation are selected within the cultivation period for genome shuffling or even after harvest, whereby the cultivation characters of the population can be led in a desirable direction.

Fixed cultivars can be bred by selecting male-fertile individuals (genotype: msms) with desired traits from the genome shuffling population during the fixation by the selfings. In even autogamous plants, applying selection pressure to the population during genome shuffling realizes an efficient recurrent selection breeding system.

Notably, since individuals with sequences introduced by a gene engineering technique are transgenic plants, the cultivation of such individuals in the field is regulated by the laws. Here, male-fertile individuals (genotype:msms) produced besides the transgenic plants contain no transgenes (foreign genes) in their genome, and thus are not genetically-modified organisms.

According to the present invention, the large population of autogamous plants can be allowed to outcross continuously without involving laborious procedures such as emasculation. Optional crossing of appropriate materials selected realizes genome shuffling thereof.

Further, by applying appropriate selection pressure and adding new breeding materials during genome shuffling, an efficient recurrent selection breeding system can be established and also cultivars derived from many breeding materials can be produced efficiently and continuously.

As illustrated in FIG. 1, a vector with the following three gene cassettes is constructed as a single construct:
1) a male-sterility gene cassette including an anther-specific promoter and a lethal gene such as a ribonuclease-encoding gene driven by the anther-specific promoter,
2) a chemical tolerance gene cassette including a constitutive promoter and a chemical tolerance gene driven by the constitutive promoter, which allows expression of genes in stems and leaves, and
3) a conditionally lethal gene cassette including an inducible promoter and a lethal gene such as a ribonuclease-encoding gene driven by the inducible promoter.

When the Agrobacterium method is employed, it is necessary to insert these gene cassettes into a vector derived from the Ti plasmid.

As the gene giving dominant male sterility and driven by the anther-specific promoter, the gene encoding Barnase with potent activity, which is a microbial ribonuclease, can be used. The Barnase-encoding gene previously achieved 100% male sterility. Besides, a protease-encoding gene or other genes achieved 100% male sterility and thus can also be used.

As the chemical tolerance gene driven by the constitutive promoter, a gene giving herbicide tolerance can be used. Notably, in general, it is necessary to use a marker gene for efficiently selecting transformants in a gene engineering technique. A hygromycin-tolerant gene cassette is generally inserted into the same construct as the above gene cassettes. In addition, when the gene encoding a modified acetolactic acid synthase (mALS) is used as the herbicide-tolerance gene, the mALS-encoding gene serves also as a marker gene, which is efficient.

The conditionally lethal gene driven by the inducible promoter can be the same as the gene giving male sterility.

In order for the marker gene not to remain in the transformant, the MAT vector may be used. Also, a Cre event may be used for removal of the marker gene. In each case, care should be taken for the selection of a vector used, since it is necessary to use a specific vector.

Using any of the vectors described above, necessary genes are introduced into plants by a gene engineering technique. The method for introducing the genes into the plants is generally the Agrobacterium method. Other methods may be used including the particle gun method and the whisker method. When the other method is employed, the vector usable is not limited to a vector derived from the Ti plasmid. In the case of rice, the Agrobacterium method can be used for protoplasts of rice.

The obtained plants are expected to have the advantages in that 1) they possess dominant male sterility, 2) only male sterile individuals can be easily selected at the seedling stage with a chemical such as an herbicide, and 3) only male-fertile individuals can be easily selected by activating the inducible promoter.

The genes for the three traits described above are provided as the single construct. Thus, when the individuals with these genes at a single locus are selected and used, the above traits are inherited in a very tight coupling linkage. Therefore, unless a large number of generations are repeated, care does not need to be taken for destroying the linkage, and no practical problems arise.

Production of transgenic plants generally gives a wide variety of transgenic plants. The produced transgenic plants are screened for individuals that normally express the genes of interest. In addition, they are screened by, for example, the southern blotting method for individuals that have the above three gene cassettes inserted at one part of the genome in a tight linkage and have no other gene fragments. These screenings ensure genetic segregation of the populations of progeny and clarification of the screening results. The resultant transgenic plants have a genotype of Ms denoting a gene symbol of male sterility in a single locus (ms denotes a gene symbol of recessive male sterility), and can be considered as having herbicide tolerance and lethality inducible by activating the inducible promoter in virtually the same locus.

There may be concerns about crossing of the produced transgenic plants with other surrounding plants. However, the above-described transgenic plants have a feature of male sterility, which means that they cannot produce pollen and hence cause undesirous gene proliferation to the surroundings as a result of pollen dispersion. Note that care should be taken for dispersion via the seeds.

Figure 2:
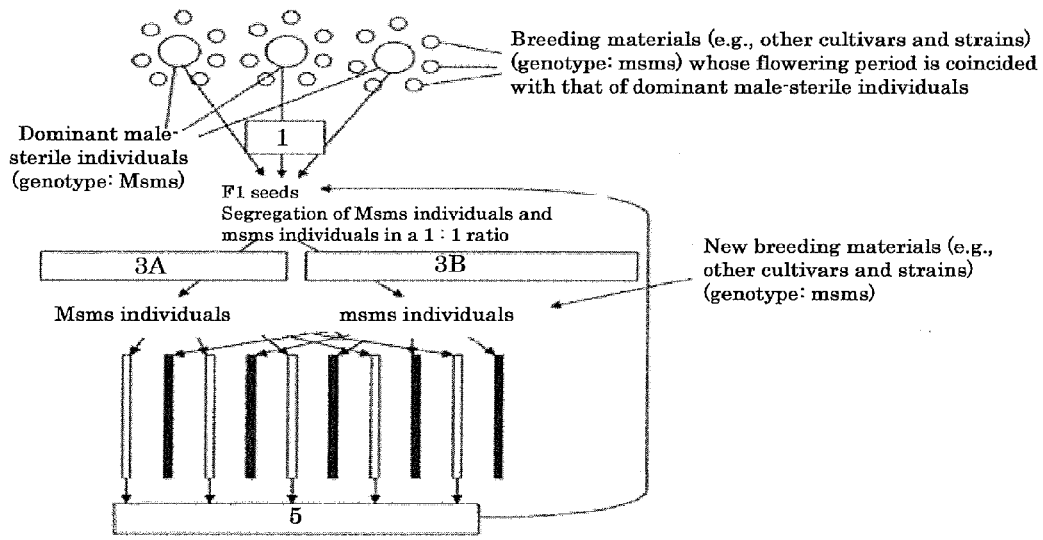
FIG. 2 schematically illustrates an efficient genome shuffling system.

As illustrated in the upper portion of FIG. 2, other cultivars or strains intended for genome shuffling are arranged near the above-described transgenic plants in their flowering periods so that the flowering period of the former coincides with that of the latter. Thereafter, seeds are harvested from the male-sterile individuals, thereby obtaining outcrossed seeds efficiently. The thus-obtained seeds are $F_1$ seeds between the transgenic plants and the other cultivars or strains intended for genome shuffling.

The obtained seeds are segregated into those with a genotype of Msms (i.e., male-sterile individuals) and those with a genotype of msms (i.e., male-fertile individuals) at a theoretical segregation ratio of 1:1. After the seeds have been split into two groups, one group is subjected to screening in terms of chemical tolerance, thereby efficiently selecting male-sterile individuals (genotype:Msms) at the seedling stage. Also, by activating the inducible promoter, it is possible to efficiently select male-fertile individuals (genotype:msms) at the seedling stage.

After the male-sterile individuals (genotype:Msms) and the male-fertile individuals (genotype:msms) have been planted in an appropriate arrangement, for example, in alternating rows, seeds are harvested from the male-sterile individuals, thereby obtaining seeds for the next generation. Sowing the obtained seeds produces the male-sterile individuals (genotype:Msms) and the male-fertile individuals (genotype: msms) at a theoretical segregation ratio of 1:1.

As illustrated in the lower portion of FIG. 2, repeating the following four steps
1) to 4) achieves continuous and efficient outcrossing in the population of autogamous plants:
1) harvesting seeds from male-sterile individuals by means of male sterility (i.e., the seeds are outcrossed seeds between the male-sterile individuals and the other cultivars) (a step indicated by reference numeral 1),
2) splitting the seeds into two groups and sowing them,
3) screening for male-sterile individuals (genotype:Msms) from the seedlings of one group by means of a chemical such as an herbicide (a step indicated by reference numeral 3A), and screening for male-fertile individuals (genotype: msms) from the seedlings of the other group by activating the inducible promoter (a step indicated by reference numeral 3B), and 4) appropriately arranging both the individuals, and letting them cross with each other.

Notably, in FIG. 2, reference numeral 5 indicates a step of efficiently harvesting outcrossed seeds.

Repeating generations fragments the genome, resulting in efficient genome shuffling without involving laborious procedures such as emasculation.

In the course of genome shuffling, the genome of the original cultivar of the male-sterile individuals accounts for 50% in theory. When new breeding materials are additionally used as male-fertile individuals (genotype: msms), such new breeding materials can be introduced into the genetic composition of the genome shuffling population, and also the ratio of the genome of the original cultivar can be decreased.

Figure 3:
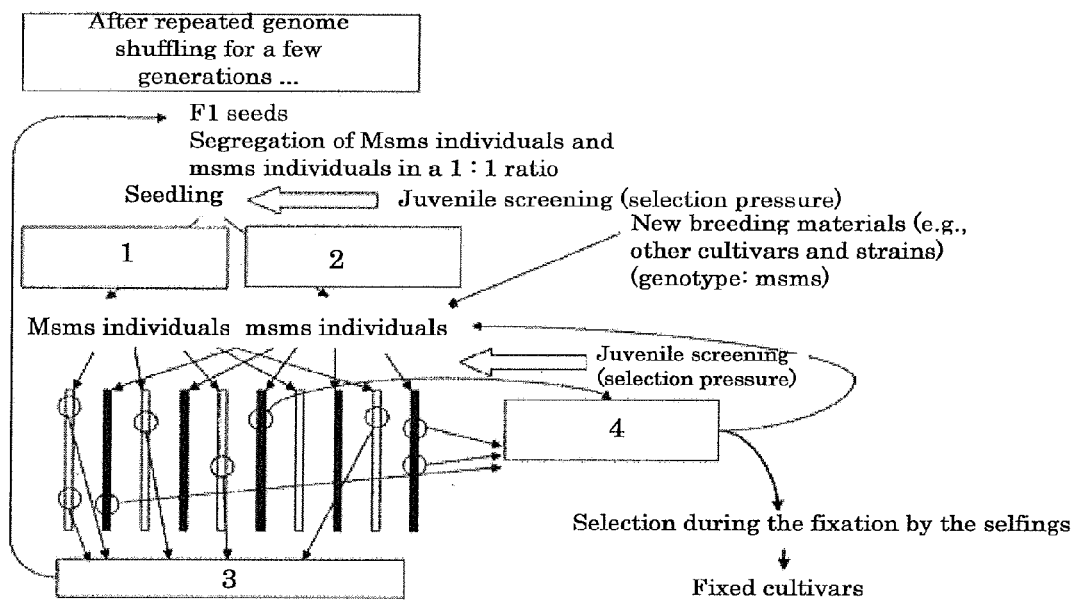
FIG. 3 schematically illustrates a recurrent selection breeding system based on genome shuffling.

As illustrated in FIG. 3, efficient genome shuffling realizes an efficient recurrent selection breeding system through application of appropriate selection pressure as well as increased genetic variability due to newly formed gene combinations. Regarding a trait which can be screened for at the very early stage, for example, at the seedling stage (e.g., disease tolerance), screening may be performed at the seedling stage after the seeds have been harvested from the male-sterile individuals, split into two groups and sown. Alternatively, such screening may be performed for the period within which screening for male-sterile or male-fertile individuals is done. Juvenile screening such as a test for disease tolerance can lead specific traits of the genome shuffling population in a desirable direction. In FIG. 3, reference numeral 1 denotes a step of screening for male-sterile individuals by means of a chemical such as an herbicide, reference numeral 2 denotes a step of screening for male-fertile individuals by activating the inducible promoter, reference numeral 3 denotes a step of efficiently harvesting outcrossed seeds, and reference numeral 4 denotes a step of harvesting seeds (mainly $F_2$ seeds) (genotype: msms) through examination of cultivation characters and application of selection pressure.

Juvenile screening may not be performed for many cultivation characters and important traits in breeding such as yield and quality. Such characters and traits must be examined within the cultivation period for genome shuffling or even after harvest. Screening during the growth period can be performed by selecting individuals with inferior traits from the population of male-sterile individuals (genotype:Msms) and male-fertile individuals (genotype:msms).

In the case where the male-sterile individuals (genotype: Msms) are screened for characters through examination after harvest, the populations of progeny are made for continuous genome shuffling while the seeds obtained from the individuals with superior characters are managed as strains. As a result, continuous genome shuffling can be performed while confirming the screening effects.

In the case where the male-fertile individuals (genotype: msms) are screened for characters through examination after harvest, it is likely that the rate of the self-fertilized seeds is high. However, the seeds of the next generation are managed as strains and can be used as pollen parents.

In this manner, applying appropriate selection pressure in the course of genome shuffling can lead the traits of the population in a desirable direction.

After genome shuffling over a few generations, male-fertile individuals (genotype:msms) are screened for individuals with superior traits, whose subsequent generations are further screened during the fixation by selfings, whereby fixed cultivars can be bred. The resultant fixed cultivars are male-fertile individuals (genotype:msms).

Notably, male-fertile individuals (msms) contain no fragments of transgenes, and thus are not gene recombinants. Therefore, such male-fertile individuals may not be regulated by the laws against genetically-modified organisms.

As described above, the genome shuffling method and the efficient recurrent selection breeding system based thereon provide a new breeding method to greatly exploit underlying possibilities of breeding in the genome of plants which are generally autogamous.

According to the present invention, dominant male-sterility obtained by, for example, a transgenic technique is utilized for allowing the populations of autogamous plants (e.g., rice and wheat) to repeatedly outcross without involving laborious procedures such as emasculation, realizing efficient genome shuffling. Applying appropriate selection pressure in the course of efficient genome shuffling realizes an efficient recurrent selection breeding system for autogamous plants, which contributes to improvements of yield and quality as crops in breeding of autogamous plants.

What is claimed is:

1. A genome shuffling method for autogamous plants, comprising:
    producing dominant male-sterile individuals by transforming a plant with a vector having the following three gene cassettes as a single constructs:
    1) a male-sterility gene cassette including an anther-specific promoter and a ribonuclease-encoding gene that is driven by the anther-specific promoter,
    2) a chemical tolerance gene cassette including a constitutive promoter and a chemical tolerance marker gene driven by the constitutive promoter, wherein the constitutive promoter allows expression of the chemical tolerance marker gene in stems and leaves, and
    3) a susceptibility gene cassette to physical environment or a specific chemical including a gene for destroying intrinsic tolerances to the environment or chemicals,
    arranging cultivars or strains intended for genome shuffling near the dominant-male sterile individuals in a flowering period of each of (1) the cultivars or strains intended for genome shuffling and (2) the dominant-male sterile individuals, so that the flowering periods of (1) and (2) coincide with one another,
    harvesting outcrossed seeds from the dominant-male sterile individuals,
    segregating the outcrossed seeds into a first group and a second group,
    subjecting the first group to screening in terms of chemical tolerance, thereby allowing selection of male-sterile individuals at the seedling stage,
    subjecting the second group to destruction of intrinsic tolerances to the environment or chemicals, thereby efficiently selecting male-fertile individuals at the seedling stage,
    arranging the male-sterile individuals and the male-fertile individuals close together in flowering periods thereof, so that the male-sterile individuals are capable of crossing with the male-fertile individuals,
    harvesting seeds from the male-sterile individuals, and
    repeating outcrossing using the seeds from generation to generation.

* * * * *